(12) United States Patent
Wall

(10) Patent No.: US 6,786,880 B2
(45) Date of Patent: *Sep. 7, 2004

(54) THERAPEUTIC PAD

(76) Inventor: Lisa Wall, 3760 NW. 173$^{rd}$ Pl., Beaverton, OR (US) 97006

( * ) Notice: Subject to any disclaimer, the term of this patent is extended or adjusted under 35 U.S.C. 154(b) by 65 days.

This patent is subject to a terminal disclaimer.

(21) Appl. No.: 10/109,167

(22) Filed: Mar. 26, 2002

(65) Prior Publication Data
US 2002/0107491 A1 Aug. 8, 2002

Related U.S. Application Data

(63) Continuation-in-part of application No. 09/370,079, filed on Aug. 6, 1999, now Pat. No. 6,320,095.

(51) Int. Cl.$^7$ .................. A61F 5/00; A61F 13/15; A61F 7/00
(52) U.S. Cl. .................. 602/2; 604/368; 604/358; 607/96; 607/108; 607/114
(58) Field of Search .................. 602/2, 41, 42, 602/43, 48; 604/368, 385.1, 385.06, 385.14, 385.19, 386, 387, 388, 396, 398, 400, 401, 402, 304–308; 128/888, 889; 607/96, 104, 108, 109, 110, 111, 112, 114

(56) References Cited

U.S. PATENT DOCUMENTS

| | | | | |
|---|---|---|---|---|
| 1,567,931 A | * | 12/1925 | Epler | 607/112 |
| 4,044,773 A | * | 8/1977 | Baldwin, III | 607/114 |
| 4,240,436 A | * | 12/1980 | Singleton | 607/108 |
| 4,530,220 A | * | 7/1985 | Nambu et al. | 62/530 |
| 4,834,737 A | * | 5/1989 | Khan | 604/385.14 |
| 4,951,666 A | * | 8/1990 | Inman et al. | 607/114 |
| 5,052,387 A | * | 10/1991 | Natali | 607/108 |
| 5,150,707 A | * | 9/1992 | Anderson | 607/114 |
| 5,167,655 A | * | 12/1992 | McCoy | 604/396 |
| 5,178,139 A | * | 1/1993 | Angelillo et al. | 607/114 |
| 5,243,974 A | * | 9/1993 | Allen | 607/108 |
| 5,277,180 A | * | 1/1994 | Angelillo et al. | 607/114 |
| 5,431,622 A | * | 7/1995 | Pyrozyk et al. | 602/2 |
| 5,534,020 A | * | 7/1996 | Cheney et al. | 607/108 |
| 5,643,189 A | * | 7/1997 | Masini | 602/58 |
| 5,702,375 A | * | 12/1997 | Angelillo et al. | 604/358 |
| 6,102,899 A | * | 8/2000 | Yimin | 604/385.01 |
| 6,320,095 B1 | * | 11/2001 | Wall | 604/368 |

* cited by examiner

Primary Examiner—Kim M. Lewis
(74) Attorney, Agent, or Firm—Chernoff, Vilhauer, McClung & Stenzel, LLP

(57) ABSTRACT

An absorbent pad has a cavity formed by a first flexible sheet of a liquid impermeable material and a second flexible sheet of a liquid permeable material. An opening defined by at least one of the first sheet and second sheet. An interior sheet of a liquid absorbent material forms a gel upon contact with a liquid.

13 Claims, 2 Drawing Sheets ial Ser. No. 09/370,079 filed Aug. 6, 1999; and claims
THERAPEUTIC PAD

CROSS-REFERENCE TO RELATED APPLICATIONS

This application claims the benefit of U.S. patent application Ser. No. 09/370,079 filed Aug. 6, 1999; and claims priority of U.S. Pat. No. 6,320,095.

BACKGROUND OF THE INVENTION

The present invention relates to a therapeutic thermal pack suitable for hazardous waste disposal.

Various types of bandages, gauze, and other types of devices including absorbing material exist for absorbing blood and other fluid discharge from the body of a patient. These devices range in size and type from very large wraps of gauze material to small bandage type absorbent material with attached adhesive material for securing the absorbent material in a fixed position relative to the area of recovery of the patient.

A particular application of specialized absorbent bandages is in the area of obstetrics and gynecology. Several bandages have been specifically contoured for comfortable positioning within the area of recovery of an obstetric or gynecological patient, especially after giving birth to a child. Obstetric and gynecological bandages are formed to be generally rectangular with indentations or recesses on the opposed sides of the bandage midpoint between the opposed ends having a general hourglass shape for a comfortable fit for the recovering obstetric or gynecological patient. Typically, the obstetric and gynecological bandages are worn within an undergarment which positions and maintains the absorbent material proximate the recovering area of the patient. In addition, gauze based bandages typically have limited absorbency.

Thermal packs proximate the recovering area for cooling or heating the recovery area provide substantial relief from pain and discomfort. For example, the thermal pack may include a flexible plastic container having a plurality of distinct chemical substances therein. Upon mixing the chemical substances, a chemical reaction takes place which undergoes an endothermic (cold pack) or an exothermic reaction (hot packs). Accordingly, the temperature of the container becomes a different temperature than the ambient temperature to provide a cooling or a heating comfort to the patient. Unfortunately, the expense of the chemical substances results in a thermal pack that is unduly expensive.

A more inexpensive alternative to the thermal pack is to employ a simple ice pack (plastic bad filled with ice) wrapped in a cloth applied to the recovering area. Unfortunately, the ice pack is difficult to maintain within the cloth, and the combination is difficult to maintain on the recovering area if the patient moves.

A further inexpensive alternative is to place ice within an exam glove, tie the end of the glove shut, and wrap the glove in a cloth. While such a modified exam glove is inexpensive, the application of such a combination is not comfortable to the patient.

In the era of deadly blood transmitted diseases, such as AIDS, the disposal of material that includes bodily fluids is a serious concern. After use of the thermal pack, a nurse puts on surgical gloves and places the thermal pack, surgical glove, cloth, and fluids absorbed therein, in a hazardous waste bag. The hazardous waste bag is sealed shut and disposed of in a hazardous waste container or dropped down a hazardous waste chute. Unfortunately, the bag periodically breaks resulting in bodily fluids contaminating the waste container or chute. If such an event occurs, the container or chute must be sterilely cleaned, which is expensive and inconvenient. In addition, such an event subjects a hospital or care provider to fines.

What is desired, therefore, is an inexpensive perineal pack and/or container for the perineal pack that is not prone to breaking.

DETAILED DESCRIPTION OF THE PREFERRED EMBODIMENT

After consideration of the limitations of the aforementioned drawbacks of the prior art devices, the present inventor initially considered techniques to decrease the likelihood that the exterior hazardous waste bag would break under impact by using a stronger waste bag. The present inventor determined that the solution to the aforementioned limitations does not rest in redesigning the hazardous waste bag itself but instead in the technique used to capture the bodily fluids and blood from the body of the patient.

Figure 1:
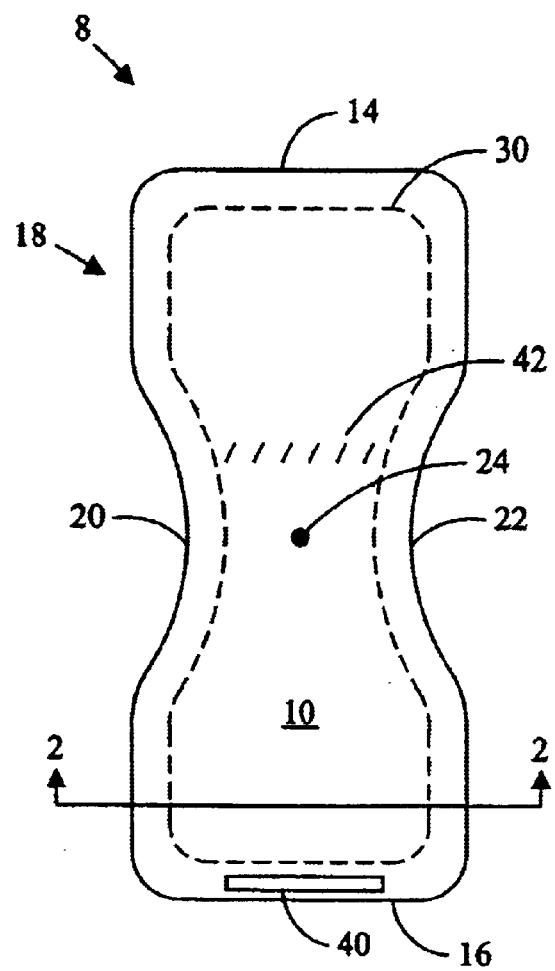
FIG. 1 is a frontal top view of an exemplary embodiment of a pad of the present invention including a gel forming material therein.
Figure 2:
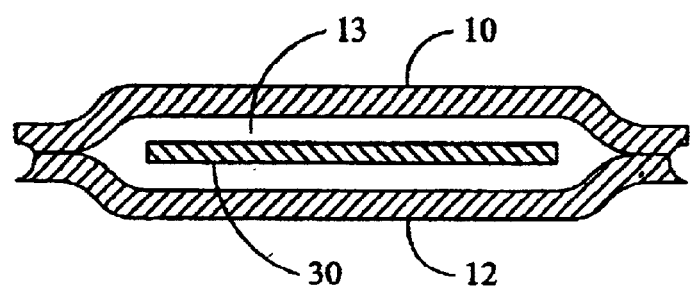
FIG. 2 is a sectional side view of the pad of FIG. 1 along line 2—2.

Referring to FIGS. 1 and 2, an exemplary embodiment of the present invention comprises an pad 8 including inner sheet 10 and an outer sheet 12 sealed around the periphery to each other. The sealing may be at locations other than the periphery such that the inner and outer sheets 10 and 12 (potentially with additional material) form a cavity 13 therein. The inner sheet 10 is fabricated from a generally flexible, liquid permeable material, such as for example, a thermo-bonded polypropylene. The outer sheet 12 is fabricated from a generally flexible, liquid impermeable material, such as for example, plastic. The pad 8 has a generally elongated dimension extending between a first end 14 and a second end 16. The pad 8 has a transverse dimension extending between a first side 18 and a second side 20. The pad 8 is preferably generally rounded at the junctures of the first and second ends 14 and 16, and the first and second sides 18 and 20, as shown.

The pad 8 preferably has a first and a second recess 20 and 22 defined in the first and second sides 18 and 20 generally midpoint between the first and second ends 14 and 16. The transverse dimension at the midpoint 24 of the first and second ends 14 and 16 is less than the transverse dimension proximate the first and second ends 14 and 16. The result is a generally "hour-glass" shaped pad 8.

An interior sheet 30 (preferably substantially flat) of liquid absorbing material is included between the inner sheet 10 and the outer sheet 12. The interior sheet 30 has an elongate dimension extending generally between the first end 14 and the second end 16, and similarly defines a transverse dimension extending generally between the first and second sides 18 and 20, respectively. In a similar manner, the interior sheet 30 is preferably generally rounded at the junctures of the first and second ends 14 and 16, and the first and second sides 18 and 20. The interior sheet 30 defines a first and a second recess generally at the midpoint 24 between the first and second ends 14 and 16. The transverse dimension of the inside and outside sheets 10 and 12 at the first and second ends 14 and 16 is less than the transverse dimension of the interior sheet 30 proximate the first and second ends 14 and 16. The interior sheet 30 preferably has a slightly smaller dimension than the exterior periphery of the pad 8.

The present inventor came the realization that the absorption and retention of bodily fluids and blood from the area of recovery of the patient is dramatically improved if the liquid absorbing interior sheet 30 forms a "gel-like" material upon contact with liquid. The creation of the gel acts to absorb and capture the bodily fluids and blood in a manner that is highly resistant to releasing the bodily fluids and blood, even under pressure. In addition, gel forming materials are highly absorbent to liquids in a manner much greater than many other materials, such as cotton based materials. One suitable gel-forming material is found in common baby diapers. Accordingly, upon locating the pad 8 in the area of recovery, the bodily fluids and blood will pass through the liquid permeable inner sheet 10 and be absorbed by the interior sheet 30. In addition, the liquid impermeable outer sheet 12 will assist in maintaining the bodily fluids and blood within the pad 8.

To provide thermal capacity, such as a cooling, the end of the pad 8 includes a sealable opening 40. Preferably, the sealable opening is such that it may be repeatedly unsealed (opened) and sealed (closed). The sealable opening 40 may take any form, such as for example, a tape sealed opening, one or more snaps, and a pair of interconnectable pieces, such as that commonly used on plastic bags. The sealable opening 4 is opened and ice or other cold materials (liquid or solid) are inserted within the cavity 13 when the pad 8 is to be used. The ice or other cold materials may be located on either side of the interior sheet 30 (or both), as desired. The ice provides an inexpensive, readily available source of cooling material. The opposing end portion of the pad from the sealable opening 40 may be blocked by any suitable structure, such as for example, a stitch 42 so that the ice or other cold materials is maintained in generally the central region of the pad 8. After inserting the ice or other cold materials, the sealable opening 40 is sealed and the pad 8 is applied to the area of recovery of the patient. While the ice or other cold materials melt, the resulting liquid is absorbed and raptured by the interior sheet 30, thereby forming a gel. This provides the effect of cooling white simultaneously preventing the escape of the liquids which would otherwise result in potential hazardous waste when commingled with bodily fluids and blood from the patient. It is noted that the preferred embodiment is free from an internal liquid impermeable enclosure for the ice or other cooling material. Alternatively, the sealable opening 40 may be located at any intermediate location between the ends of the pad 8 on either side or between the inner and outer sheets 10 and 12.

To provide thermal capacity, such as a cooling, the end of the pad 108 includes a sealable opening 140. Preferably, the sealable opening is such that it may be repeatedly unsealed (opened) and sealed (closed). The sealable opening 140 may take any form, such as for example, a tape sealed opening, one or more snaps, and a pair of interconnectable pieces, such as that commonly used on ZIPLOCK plastic bags. The sealable opening 140 may be the opening defined by the end of the inside and outside sheets 110 and 112. A removable strip 175 with adhesive 177 thereunder on the outside of sheet 110 may be partially pulled back or totally removed.

The outer sheet 112, with the inner sheet tucked therein may be adhered to the adhesive 177 to close the opening 140. It is noted that the opening may only be partially sealed, though the partial sealing acts to "seal" the opening 140 or otherwise at least partially inhibit the flow of liquid or other materials from within the cavity 113. The sealable opening 140 is opened and ice or other cold materials (liquid or solid) are inserted within the cavity 113 when the pad 108 is to be used. The ice or other cold materials may be located on either side of the interior sheet 130 (or both), as desired. The ice provides an inexpensive, readily available source of cooling material. The opposing end portion of the pad from the sealable opening 140 may be blocked by any suitable structure, such as for example, a stitch 142 or bonding a portion of the inner and outer sheet together so that the ice or other cold materials is maintained in generally the central region of the pad 108. After inserting the ice or other cold materials, the sealable opening 140 is sealed and the pad 108 is applied to the area of recovery of the patient. While the ice or other cold materials melt, the resulting liquid is absorbed and captured by the interior sheet 130, thereby forming a gel. This provides the effect of cooling while simuultaneously preventing the escape of the liquids which would otherwise result in potential hazardous waste when commingled with bodily fluids and blood from the patient. It is noted that the preferred embodiment is free from an internal liquid impermeable enclosure for the ice or other cooling material. Alternatively, the sealable opening 140 may be located at any intermediate location between the ends of the pad 108 on either side or between the inner and outer sheets 110 and 112.

After use, the nurse puts on gloves and places the pad 8 in a hazardous waste bag. The hazardous waste bag is then disposed of properly. Without any significant volume of unabsorbed liquid, even if the hazardous waste bag was to break, there would likely be no discharge of liquids requiring cleanup or violations of the environmental regulations.

Figure 3:
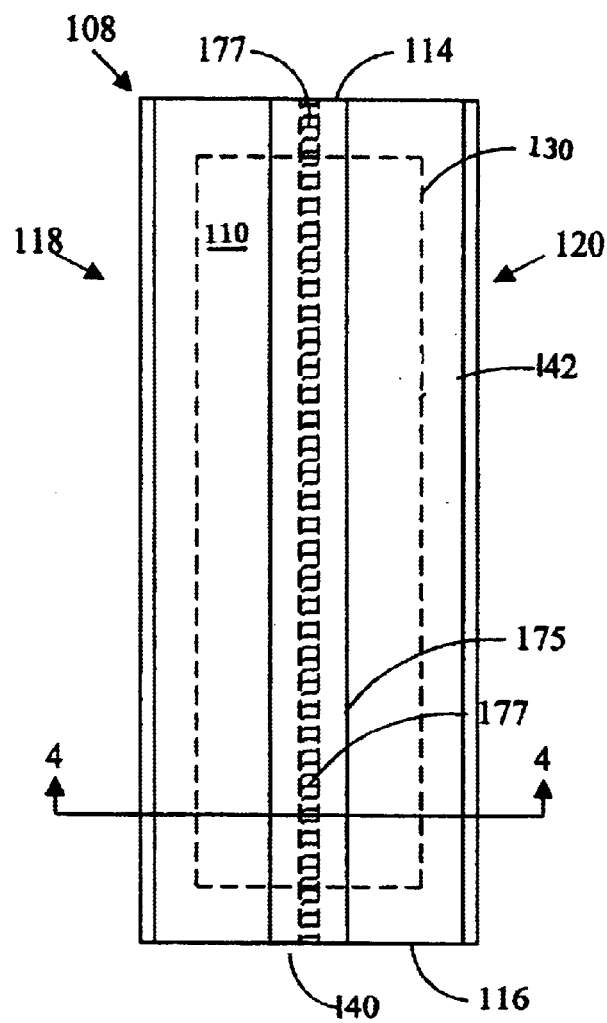
FIG. 3 is a frontal top view of another exemplary embodiment of a pad of the present invention including a gel forming material therein.
Figure 4:
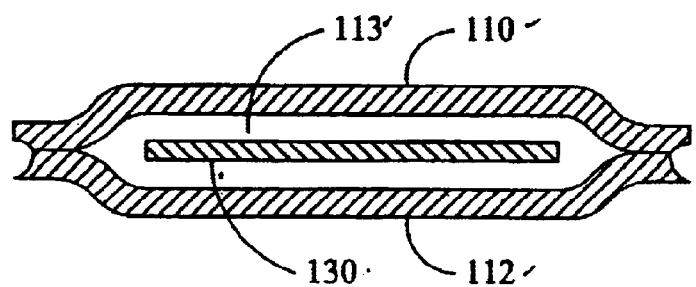
FIG. 4 is a sectional side view of the pad of FIG. 3 along line 4—4.

Referring to FIGS. 3 and 4, another exemplary embodiment of the present invention comprises a pad 108 including inner sheet 110 and an outer sheet 112 sealed around the periphery to each other. The sealing may be at locations other than the periphery such that the inner and outer sheets 110 and 112 (potentially with additional material) form a cavity 113 therein. The inner sheet 110 is fabricated from a generally flexible, liquid permeable material, such as for example, a thermo-bonded polypropylene. The outer sheet 112 is fabricated from a generally flexible, liquid impermeable material, such as for example, plastic. The pad 108 has a generally elongated dimension extending between a first end 114 and a second end 116. The pad 108 has a transverse dimension extending between a first side 118 and a second side 120.

The pad 108 preferably has a substantially straight first and second sides 118 and 120. The result is a generally "rectangular" shaped pad 108.

An interior sheet 130 (preferably substantially flat) of liquid absorbing material is included between the inner sheet 110 and the outer sheet 112. The interior sheet 130 has an elongate dimension extending generally between the first end 114 and the second end 116, and similarly defines a transverse dimension extending generally between the first and second sides 118 and 120, respectively. The transverse dimension of the inside and outside sheets 110 and 112 at the first and second ends 114 and 116 is greater than the transverse dimension of the interior sheet 130 proximate the first and second ends 114 and 116. The interior sheet 130 preferably has a slightly smaller dimension than the exterior periphery of the pad 108.

The liquid absorbing interior sheet 130 preferably forms a "gel-like" material upon contact with liquid. The creation of the gel acts to absorb and capture the bodily fluids and blood in a manner that is highly resistant to releasing the bodily fluids and blood, even under pressure. In addition, gel forming materials are highly absorbent to liquids in a manner much greater than many other materials, such as cotton based materials. One suitable gel-forming material is found in common baby diapers. Accordingly, upon locating the pad 108 in the area of recovery, the bodily fluids and blood will pass through the liquid permeable inner sheet 110 and be absorbed by the interior sheet 130. In addition, the liquid impermeable outer sheet 112 will assist in maintaining the bodily fluids and blood within the pad 108.

After use, the nurse puts on gloves and places the pad 108 in a hazardous waste bag. The hazardous waste bag is then disposed of properly. Without any significant volume of unabsorbed liquid, even if the hazardous waste bag was to break, there would likely be no discharge of liquids requiring cleanup or violations of the environmental regulations.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

What is claimed is:

1. A method of treating an area of recovery of a patient comprising the steps of:
   (a) providing a pad defining a cavity therein formed by a first flexible sheet of a liquid impermeable material and a second flexible sheet of a liquid permeable material enclosing an interior sheet of a liquid absorbent material that forms a gel upon contact with a liquid;
   (b) inserting a cold material through an at least partially sealable opening formed in said pad;
   (c) at least partially sealing said opening;
   (d) treating said patient with said pad to said area of recovery such that at least one of bodily fluids and blood from said patient is absorbed by said interior sheet of said pad forming said gel.

2. The method of claim 1 further comprising forming said gel together with liquid from said cold material.

3. The method of claim 2 wherein said cold material is ice.

4. The method of claim 3 wherein said cavity is formed by joining the periphery of said first sheet and said second sheet together.

5. The method of claim 1 wherein said sealable opening is proximate one end of said pad.

6. The method of claim 1 wherein said sealable opening defines an opening directly to said interior sheet.

7. The method of claim 6 wherein said pad is free from a liquid impermeable sealed enclosure within said first and second sheet.

8. The method of claim 1 wherein at least one of said first flexible sheet and said second flexible sheet is rounded at least one end thereof.

9. The method of claim 1 wherein at least one of said first flexible sheet and said second flexible sheet is narrower at the midpoint of the length of said respective first flexible sheet and said second flexible sheet than at the respective end thereof.

10. The method of claim 1 wherein said interior sheet is substantially flat.

11. The method of claim 1 wherein said pad is generally hour-glass shaped.

12. The method of claim 1 wherein said sealable opening is sealed after inserting said cold material.

13. The method of claim 12 wherein said pad is disposed of in a hazardous waste manner.

\* \* \* \* \*

UNITED STATES PATENT AND TRADEMARK OFFICE
CERTIFICATE OF CORRECTION

| | | |
|---|---|---|
| PATENT NO. | : 6,786,880 B2 | Page 1 of 1 |
| APPLICATION NO. | : 10/109167 | |
| DATED | : September 7, 2004 | |
| INVENTOR(S) | : Lisa Wall | |

It is certified that error appears in the above-identified patent and that said Letters Patent is hereby corrected as shown below:

Col. 1, Line 50

Change "(plastic bad filled with ice)" to read: --(plastic bag filled with ice)--.

Col 3, Line 47

Change "and raptured by the" to read: --and captured by the--;

Col. 3, Line 48

Change "effect of cooling white simultaneously" to read: --effect of cooling while simultaneously--.

Col. 4, Line 25

Change "free from an intermal" to read: --free from an internal--.

Signed and Sealed this
Eighth Day of May, 2012

David J. Kappos
*Director of the United States Patent and Trademark Office*